United States Patent
Riesinger

(10) Patent No.: US 10,925,773 B2
(45) Date of Patent: Feb. 23, 2021

(54) WOUND CARE ARTICLE HAVING SUPER-ABSORBENT FIBERS AND SUPER-ABSORBENT PARTICLES

(71) Applicant: BSN MEDICAL, GMBH, Hamburg (DE)

(72) Inventor: Birgit Riesinger, Münster (DE)

(73) Assignee: BSN medical GmbH, Hamburg (DE)

( * ) Notice: Subject to any disclaimer, the term of this patent is extended or adjusted under 35 U.S.C. 154(b) by 356 days.

(21) Appl. No.: 15/008,105

(22) Filed: Jan. 27, 2016

(65) Prior Publication Data
US 2016/0270966 A1 Sep. 22, 2016

Related U.S. Application Data

(63) Continuation of application No. PCT/EP2014/067282, filed on Aug. 12, 2014.

(30) Foreign Application Priority Data

Aug. 12, 2013 (DE) ...................... 10 2013 108 734.5
Oct. 31, 2013 (DE) ...................... 20 2013 104 893.3

(51) Int. Cl.
| | | |
|---|---|---|
| A61F 13/02 | (2006.01) |
| A61L 15/24 | (2006.01) |
| A61F 13/00 | (2006.01) |
| A61L 15/60 | (2006.01) |
| A61L 15/28 | (2006.01) |
| A61L 15/58 | (2006.01) |
| A61M 1/00 | (2006.01) |

(52) U.S. Cl.
CPC .... *A61F 13/0209* (2013.01); *A61F 13/00063* (2013.01); *A61F 13/00068* (2013.01); *A61F 13/022* (2013.01); *A61F 13/025* (2013.01); *A61L 15/24* (2013.01); *A61L 15/28* (2013.01); *A61L 15/58* (2013.01); *A61L 15/60* (2013.01); *A61F 2013/00357* (2013.01); *A61M 1/0088* (2013.01)

(58) Field of Classification Search
CPC .......... A61F 13/02; A61F 13/00; A61M 1/00; A61L 15/28; A61L 15/60; A61L 15/24
USPC ........................................................ 604/319
See application file for complete search history.

(56) References Cited

U.S. PATENT DOCUMENTS

| | | | |
|---|---|---|---|
| 2002/0007166 A1* | 1/2002 | Mitchell ................ | D21H 21/22 604/368 |
| 2003/0149413 A1 | 8/2003 | Mehawej | |

(Continued)

FOREIGN PATENT DOCUMENTS

| | | | | |
|---|---|---|---|---|
| CN | 1627927 A | 6/2005 | | |
| EP | 1 507 498 | 7/2009 | ............. | A61F 13/02 |

(Continued)

OTHER PUBLICATIONS

International Preliminary Report on Patentability issued in corresponding foreign application, PCT/EP2014/067282, pp. 1-8 (dated Feb. 16, 2016).

(Continued)

*Primary Examiner* — Andrew J Mensh
(74) *Attorney, Agent, or Firm* — Rankin, Hill & Clark LLP

(57) ABSTRACT

The invention relates to a wound care article relates having at least one flat layer consisting of a woven fabric or nonwoven comprising superabsorbent fibers and superabsorbent particles.

17 Claims, 1 Drawing Sheet

(56) References Cited

U.S. PATENT DOCUMENTS

2005/0136773 A1* 6/2005 Yahiaoui ............... A61F 13/537
            442/394
2011/0136986 A1* 6/2011 Elliott .................... A61L 15/60
            525/329.8

FOREIGN PATENT DOCUMENTS

| WO | WO 2013/026879 | 2/2013 | ............. A61L 15/46 |
| WO | WO 2013/026912 | 2/2013 | ............. A61L 15/46 |

OTHER PUBLICATIONS

International Search Report issued in corresponding foreign application, PCT/EP2014/067282, pp. 1-3 (dated Feb. 15, 2015).
Written Opinion issued in corresponding foreign application, PCT/EP2014/067282, pp. 1-7 (dated Feb. 15, 2015).
Chinese Office Action dated May 31, 2019 for the corresponding Chinese Patent Application No. 201480056100.4; English translation of cover page only.

* cited by examiner

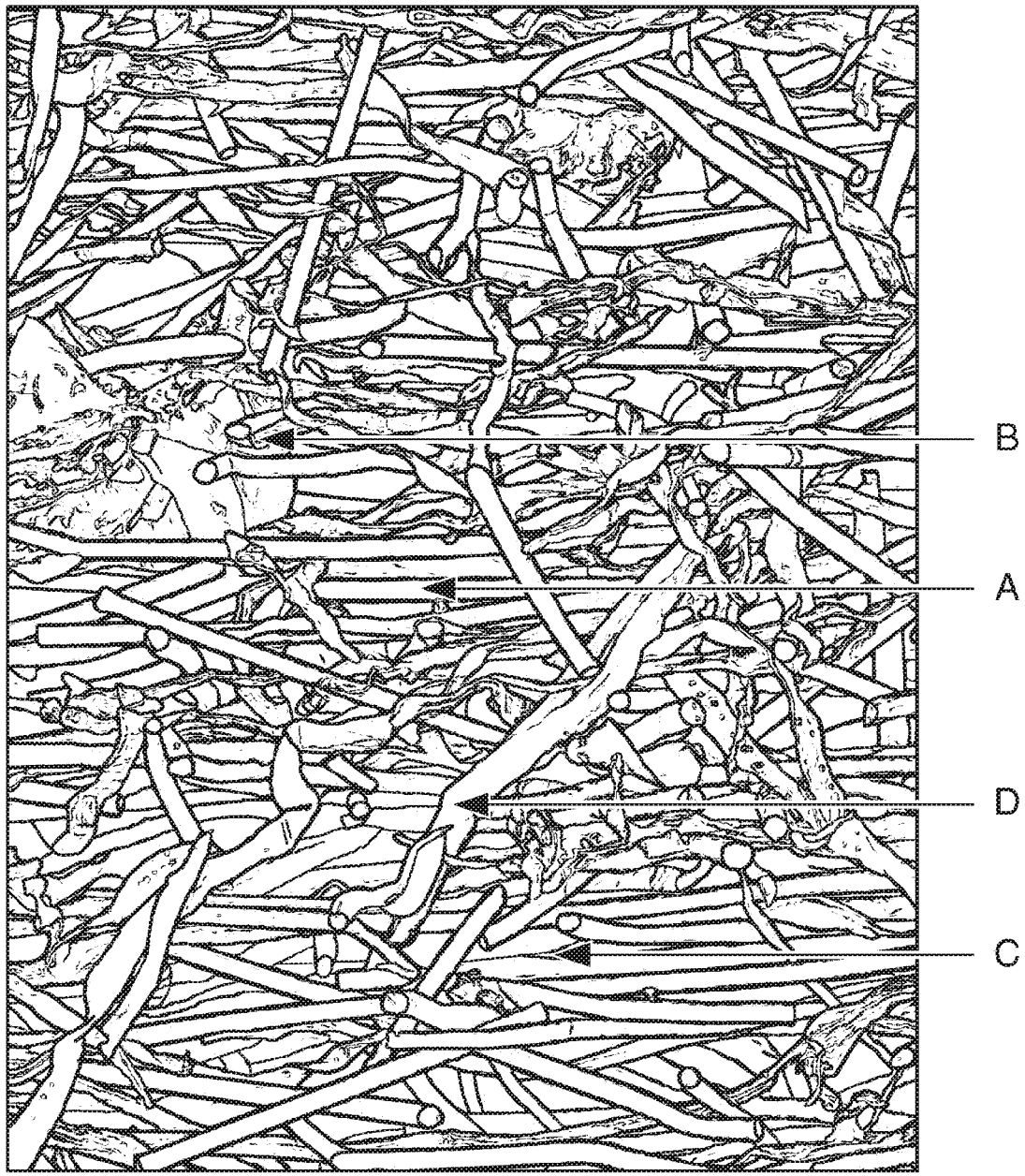

WOUND CARE ARTICLE HAVING SUPER-ABSORBENT FIBERS AND SUPER-ABSORBENT PARTICLES

CROSS-REFERENCE TO RELATED APPLICATIONS

The present invention is a continuation and claims priority under 35 U.S.C. § 120 and § 365(c) to PCT International Patent Application PCT/EP2014/067282, filed Aug. 12, 2014; which claims priority to German Patent Application No. 10 2013 108 734.5, filed Aug. 12, 2013 and German Patent Application No. 20 2013 104 893.3, filed Oct. 31, 2013, all of which are herein incorporated by reference in their entireties.

BACKGROUND

The present invention relates to a wound care article having superabsorbent fibers and superabsorbent particles.

Wound care articles having superabsorbent polymers are known, for example, from European patent EP 1507498 and have proven their worth in the care of chronic and highly exuding wounds. In these wound care articles, superabsorbent polymer particles are incorporated into a cellulose matrix.

The relatively small percentage by weight of superabsorbent polymers (although it is sometimes over 60% by weight) resulting from this approach can prove to be disadvantageous for certain areas of application and indications.

Moreover, the conventional wound dressings have a certain stiffness and low flexibility, which is a drawback, for example, in the case of deep wounds, among other things, because contact with the wound bed cannot always be ensured. This stiffness is ultimately due to the often very high density of such wound dressings or of their inner layers.

Likewise, in conventional wound dressings, under certain circumstances, the absorbed fluid can be distributed horizontally, which entails the risk of maceration of the wound edge.

The objective of the present invention is to put forward a wound care article that does not exhibit these drawbacks.

SUMMARY OF THE INVENTION

This objective is achieved by the features of the presented main claim.

The subject matter of the invention is a wound care article having at least one flat layer consisting of a woven fabric or nonwoven comprising
  superabsorbent fibers and
  superabsorbent particles.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying FIGURES, like elements are identified by like reference numerals among the several preferred embodiments of the present invention.

FIG. 1 shows a nonwoven according to the invention in a scanning electron microscope image.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The term "wound care article" will refer below especially to a wound dressing, preferably a flat wound dressing, or a wound care bandage. This wound dressing comprises a flat layer and can be configured so as to be absorbent or non-absorbent or hardly absorbent. In particular, the term "wound care article" can also be used to refer to an array of products that are placed in a certain arrangement on the wound that is to be treated. This array can form a physical unit in that the various products are combined in a shared sheath or—if applicable, without a sheath—are adhesively bonded to each other. However, the array can also be available in the form of a kit in which the various products are placed onto the wound that is to be treated in the given arrangement by means of a wrapper.

The term "nonwoven" refers to a flat textile structure made up of individual fibers that, in contrast to wovens, knits and knitted fabrics, is not made up of filaments. Due to the adhesion of the individual fibers to each other, as a rule, nonwovens retain their structural integrity. These nonwovens are also referred to as "web structures" and are produced, for example, by milling the fibers. The term "airlaid" refers to a special nonwoven made of cellulose and polyolefin fibers in which, if applicable, superabsorbent polymers have been embedded.

The term "exudate" refers to a fluid that has escaped from the wound because of inflammatory processes of the blood plasma. By the same token that the blood is responsible for the transport of nutrients and other semiochemicals, thereby supplying various parts of the body, the exudate serves in a very similar manner to supply the wound bed and the healing processes that are taking place there. In order to fulfill these numerous functions, the exudate contains a wide array of components, resulting in a specific weight that is slightly above that of water. In this way, it also differs from a transudate which comes from non-inflammatory processes and which has a much lower specific weight as well as a low cell and protein content. Aside from providing nutrients for the fibroblasts and epithelial cells, due to its high content of growth factors and cytokines, the composition of the exudate influences the various processes of wound healing in terms of time and space. They are formed primarily by thrombocytes, keratinocytes, macrophages und fibroblasts. They influence the motility, the migration and the proliferation of the various cells that are involved in wound healing. Thus, the migration of cells into the wound bed is promoted and so is the supply of the newly formed granulation tissue by means of angiogenesis. The exudate also assists in the cleaning of the wound. It contains various serine, cysteine and aspartate proteases as well as matrix metalloproteases whose activity irreversibly degrades damaged tissue in a strictly regulated process, thereby preparing the wound bed for the subsequent phases of the healing process. In general, a distinction is made in such processes between a physiological and a pathological exudate.

Components of the physiological exudate are especially salts, glucose, cytokines and growth factors, plasma proteins, proteases (particularly matrix metalloproteases), granulocytes und macrophages.

Thanks to its fiber properties, the wound care article according to the invention combines the properties of three different categories of wound care articles that are currently available on the market:

- its absorption capacity is about as high as that of wound care products that have an airlaid mat containing a cellulose nonwoven with embedded superabsorbent particles (for example, the product "sorbion sachet" made by Sorbion GmbH & Co KG), as a result of which it is also suitable for highly exuding wounds as well as for wounds caused by deep edema,
- its surface moisture and cushioning are about as high as those of a foam bandage (for example, the product "Allevyn Adhesive Foam" made by Smith & Nephew), as a result of which it has a lower tendency to dry out the wound while offering a high level of comfort for the patient. In particular, the fluffy fiber structure that traps a great deal of air is responsible for the softness,
- in the same manner as a bandage containing fibers made of carboxymethyl cellulose ("Hydrofiber", for example, the product "Aquacel" made by ConvaTec), it also entails a vertical absorption of fluid associated with a markedly reduced lateral distribution of fluid, so that (i) maceration of the wound edge is prevented, and (ii) the article is able to conform to the contour of the wound ("macro-contouring").

Such a product containing a wound care article according to the invention is commercially available, for instance, under the brand name "sorbion soft".

It is preferably provided for the superabsorbent fibers to have a cross-linked polymer made up at least of the monomer constituents acrylic acid or acrylate ("AA") that is partially neutralized to form sodium salt ("AA-Na"),
methylacrylate or methylacrylic acid ("MA"), and
special acrylate/methylacrylate monomer ("SAMM"),
whereby the cross-linking between the individual polymer chains is configured as ester bonds between the acid groups of the acrylic acid or of the methylacrylate and the partial sodium salt.

The general structural formula is as follows:

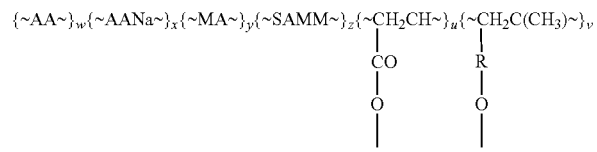

whereby the abbreviations are as follows:

| AA | stands for | CH2CH(COOH)— |
|---|---|---|
| MA | stands for | CH2CH(COOCH3)— |
| AANa | stands for | CH2CH(COOCNA)— |
| R | stands for | COOCH2CH(CH3)— |

In the case of the special acrylate/methacrylate monomer ("SAMM"), it is preferably a monomer selected from the group containing hexapropylene glycol monomethacrylate,
2-hydroxyethyl (meth)acrylate,
polyethylene glycol monomethacrylate
glycidyl methacrylate,
allyl glycidyl ether,
hydroxypropyl methacrylate, and/or
hydroxyethyl methacrylate.

Among these substances, special preference is given to hexapropylene glycol monomethacrylate.

The values of W, X, Y and Z determine the fractions of the starting materials, whereas the values of U and V depend on the temperature during the production process.

The quantitative composition can preferably be as follows (figures in mol-%):

| Component | Preferred | Very preferred | Especially preferred |
|---|---|---|---|
| AA | 30-80 | 40-70 | 58.5 |
| AANa | 10-30 | 15-25 | 19.5 |
| MA | 10-30 | 15-25 | 20 |
| SAMM | 0.5-4 | 1-3 | 2 |

Together with the other above-mentioned fibers, said fibers can be made into an airlaid product. The term "airlaid" refers to a special nonwoven in which, if applicable, superabsorbent polymers are embedded. Here, the following technologies are used, which are fundamentally known to the person skilled in the art:

MBAL=multi-bonded airlaid
BBAL/LBAL=binder-bonded airlaid/latex-bonded airlaid
HBAL/XBAL=hydrogen-bonded airlaid/X-bonded airlaid
spun-bound methods
wet-laid methods The term "superabsorbent polymers" (SAP) refers to synthetics that are capable of absorbing fluids amounting to a multiple—up to 1000 times—of their own weight. Chemically speaking, these are copolymers of acrylic acid (propenic acid, C3H4O2) and sodium acrylate (sodium salt of acrylic acid, NaC3H3O2), whereby the ratio of the two monomers to each other can vary. In addition, a so-called core cross-linker (CXL) is added to the monomer solution and it connects ("cross-links") the formed long-chain polymer molecules to each other in certain places by means of chemical bridges. These bridges render the polymer water-insoluble. When water or aqueous salt solutions penetrate the polymer particles, the polymer swells and strengthens this network on the molecular level, so that the water can no longer escape unassisted.

As an alternative, the selected superabsorbers can be on the basis of methyl acrylic acid, polyvinyl alcohol maleic acid anhydride copolymers, polysaccharide maleic acid anhydride copolymers, maleic acid derivatives, acrylamidopropane sulfonic acid copolymers, starch acrylonitrile graft polymers, gelatinized starch derivatives, alkyl or hydroxyalkyl celluloses, carboxymethyl celluloses, starch acrylic acid graft polymers, vinyl acetate acrylic acid ester copolymers, acrylonitrile or acrylamide copolymers.

The superabsorbent particles can be present in the form of a powder or as granules having a particle size between 100 μm and approximately 1000 μm.

By the same token, the above-mentioned superabsorbent polymers can also be hydrogel nanoparticles having hydroxy-terminated methacrylate monomers, such as 2-hydroxyethyl methacrylate (HEMA) and/or 2-hydroxypropyl methacrylate (HPMA), which is commercially available, for instance, as Altrazeal.

The wound care article finished in this manner has numerous advantages.

The combination of the various superabsorbent materials permits a rapid absorption of fluids without a horizontal channeling of the fluid in the widthwise direction. Here, on the one hand, exactly as in the case of carboxymethyl cellulose, a gel-moist wound contact surface is generated that, among other things, has a cooling effect and creates a healing-conducive environment, but at the same time, thanks to the absence of the horizontal channeling, it prevents moisture contact with the wound edges and the associated maceration of the wound edge.

Moreover, without the need for any further treatment steps, the wound care article according to the invention is already very soft and adaptable, it has a pleasant hand that patients subjectively perceive as pleasant, and, objectively speaking, it also offers major advantages since it counteracts trauma when the bandage is changed, it conforms to the wound contour and, at the same time, it reduces the pain perception of patients. An additional advantageous aspect is the cushioning effect that comes to the force, especially within the scope of compression or vacuum therapy. Furthermore, in this manner, the wound care article can also fill up tissue gaps or substance defects ("wound insert"), whereby, in such a case, it can be provided for the wound care article not to extend beyond the wound edge.

Particularly the conformity to the wound contour is very advantageous since, in this manner, it can be ensured that the wound care article can make direct contact with the wound bed and with the exudate that is present there. This ensures a rapid absorption and elimination of the exudate.

Moreover, the wound care article according to the invention has strong antimicrobial properties that, on the one hand, are due to the property of the superabsorbers to bind proteins and bacteria and that, on the other hand, can be ascribed to their water-binding properties which are responsible for withdrawing the fluid needed by the bacteria for their activity.

Furthermore, it is ensured that the product retains its structural integrity, even after absorbing large amounts of exudate, and it can be removed in one piece from the wound.

Moreover, it could be shown that the combination of the various superabsorbent materials permits a modulation of pro-inflammatory factors such as matrix metalloproteases ("MMPs"), oxygen radicals ("ROS") IL-1β, IL-6, IL-8 and TNFα. This effect can also be ascribed to the binding properties of the superabsorbent polymers vis-à-vis proteins.

Moreover, such a product also has a layer-dissolving effect. This is especially true of biofilms and fibrinous layers.

Owing to the above-mentioned properties, the wound care article according to the invention is suitable for numerous new indications. In particular, the wound care article according to the invention is suitable to treat acute and post-intervention wounds, chronic wounds such as, for example, diabetic wounds or pressure ulcers, tumor wounds, burns, slightly to highly exuding wounds, as well as deep wounds that might need defect filling.

It is especially preferably for the flat layer to also comprise
cellulose fibers and/or
bi-component fibers.

Said cellulose fibers can preferably be present in the form of so-called fluff pulp and, in addition to cushioning properties, they also have fluid-binding as well as structure-retaining properties.

The bi-component fibers are preferably the kind of fibers that facilitate a thermobonding of the flat layer. Therefore, they preferably contain a fraction of a thermoplastic polymer with a relatively low melting point that is made, for instance, of polyester, polypropylene or polyethylene which melts when heated up, thereby functioning as a hot-melt adhesive (hotmelt).

This is also advantageous since, in this manner, the compression of the mat at high pressure, heat and humidity (for example, by means of calandering) that is needed for conventional hydrogen bonding, as is used in airlaid products without these fibers, is made visible. Calandering results in a high degree of compaction of the mat, thereby impairing its fluffiness. Consequently, the use of these fibers increases the inclusion of air in the mat, which, in turn, leads to a faster absorption of the wound fluid owing to the capillary effect that sets in. Said bi-component fibers are preferably produced by means of co-extrusion of two polymers having different physical-chemical properties. Preference is given here to the use of the "sheath/core configuration" in which the low-melting component is on the outside while the high-melting component is on the inside, and also to the use of the "side-by-side configuration" in which the two components are in a semicircular arrangement relative to each other in the cross section of the fibers.

| Example | Sheath | Core |
|---|---|---|
| 1 | copolyester (melting point 110° C. to 120° C. | polyester (melting point 250° C.) |
| 2 | polyethylene (melting point 130° C.) | polyester (melting point 250° C.) |
| 3 | polyethylene (melting point 130° C.) | polypropylene (melting point 175° C.) |

As an alternative, it can be provided for the bi-component fibers to contain not only a thermoplastic polymer, but also a compound consisting of at least one thermoplastic base polymer and at least one superabsorbent polymer (SAP). In this context, the melting point of the first-mentioned polymer is preferably at least 20° C. higher than the melting point of the thermoplastic contained in the compound.

The table below shows compositions of a preferred flat layer by way of example. In this context, the value ranges are to be understood as also including the numerical value that delimits the value ranges.

| Component | Preferred | Very preferred | Especially preferred |
|---|---|---|---|
| Cellulose fiber | 10%-35% by weight | 150%-30% by weight | 20%-25% by weight |
| Bi-component fibers | 0.5%-15% by weight | 1%-10% by weight | 3%-8% by weight |
| Superabsorbent | 15%-60% | 20%-50% | 30%-40% |

-continued

| Component | Preferred by weight | Very preferred by weight | Especially preferred by weight |
|---|---|---|---|
| fibers | | | |
| Superabsorbent particles | 15%-60% by weight | 20%-50% by weight | 30%-40% by weight |

Fundamentally, it can be stated that the cellulose fibers absorb fluid very quickly, but that they have a relatively low absorption capacity and do not have a wicking effect.

In contrast, bi-component fibers absorb practically no fluid, but they exhibit a strong wicking effect.

Superabsorbent fibers need some time to absorb fluid, but then they have a very high absorption capacity. In the initial phase, they have a very strong wicking effect, but this diminishes rapidly as the absorption process sets in.

Consequently, a systematic selection of the quantitative fiber composition can very precisely control the absorption and fluid distribution behavior in the individual layers of the wound care article according to the invention.

Thus, for example, the outer layers can be configured in such a way that they exhibit a weak wicking effect, for example, in order to prevent maceration of the wound edge, whereas the inner layers can be configured in such a way that they exhibit a strong wicking effect so as to permit a distribution of the absorbed fluid over a large surface area.

Below, the terms "weak wicking effect", "moderate wicking effect", and "strong wicking effect" are quantified as so-called "vertical wicking height [cm/h]" by way of example.

| weak wicking effect | moderate wicking effect | strong wicking effect |
|---|---|---|
| 0.1-1 cm/h | 1-5 cm/h | 10-100 cm/h |

The table below shows properties by way of example of a preferred flat layer. In this context, the value ranges are to be understood as also including the numerical value that delimits the value ranges.

| Parameter | Preferred | Very preferred | Especially preferred |
|---|---|---|---|
| Weight per unit area (g/m$^2$) | 100-900 | 450-750 | 550-660 |
| Thickness (mm) | 1-10 | 2-8 | 3.5-4.5 |
| Absorption capacity for 0.9% saline solution (g/g) | 10-100 | 20-70 | 30-40 |
| Absorption capacity for demineralized water (g/g) | 40-400 | 60-200 | 80-100 |

Here, it is preferably provided for the flat layer to be thinner in the edge area, that is to say, for example, that its cross section at the edges is conically tapered. This ensures that there is less material at the edges of the wound.

Moreover, it is preferably provided for the flat layer to be lined or underlined with a thin nonwoven on at least one side. This can be, for instance, a thin, water-permeable web made of polypropylene, polyethylene or polyester. By the same token, this nonwoven can be a cellulose web.

Fundamentally, it can be provided for the above-mentioned nonwoven, especially if it consists of a material that tends to be hydrophobic, to be treated with a so-called avivage which leads to an improved wettability and thus allows the fluid to pass through more readily. This avivage, however, might be detrimentally affected by the subsequent calandering process.

Since the airlaid process involves blowing fibers from above onto the nonwoven, a state will initially exist in which a few fibers penetrate the nonwoven vertically. This state can be desirable since these fibers then make it easier for the fluid to enter the mat, thereby at least partially compensating for the above-mentioned detrimental effect on the avivage.

However, here, too, it is the case that preference is given to the most ideal possible symmetry of the layer structure. If—after several fiber layers have been applied during the manufacturing process—a nonwoven is used that forms a seal at the top, then there is a risk that the uppermost layer will not be penetrated by the vertically oriented fibers. This can lead to a situation in which said top sealing nonwoven offers more resistance to the fluid than the bottom nonwoven. For this reason, it can be provided for the top nonwoven—before it is applied—to undergo an abbreviated airlaid process in which fibers are blown onto the top nonwoven so as to incorporate vertically oriented fibers that penetrate the nonwoven and that allow the fluid to pass through more readily.

The weight per unit area is preferably in the range between 2 g/m$^2$ and 50 g/m$^2$, preferably between 5 g/m$^2$ and 20 g/m$^2$, especially preferably between 15 g/m$^2$ and 18 g/m$^2$. Such a nonwoven improves the structural cohesion of the layer, especially after it has absorbed fluid.

Furthermore, it is preferably provided for the superabsorbent fibers, the cellulose fibers and/or the bi-component fibers to form a matrix. It is also preferable for the superabsorbent particles to be embedded in this matrix.

Especially preferably, it is also provided for the wound care article according to the invention to have a symmetrical layer structure. The symmetrical layer structure yields a symmetrical cross section for the wound care article. This is very advantageous for daily clinical practice since, in this case, the care-taking personnel can apply the wound care article to the wound without having to pay attention to the correct orientation. There is a fundamental difference here from hygiene articles such as, for example, sanitary napkins, incontinence pads or diapers, which have a clear-cut polarity in that there is always one side facing outwards and one side facing the body.

The symmetrical layer structure makes high demands on the manufacturing process. Wound care articles of this type are often produced by means of the so-called airlaid process. Here, the fibers that are going to be used (in this case, superabsorbent fibers and, if applicable, bi-component fibers as well as cellulose fibers) are blown onto a sheet by a stream of air from above. As a rule, several series-connected blowing devices are used for this purpose. An inherent aspect of the blowing process is that the fibers applied by the second, third or other blowing devices have the tendency to migrate downwards. As a result, the fibers are redistributed, which can have a negative impact on the desired symmetry. Therefore, it can be desirable for such a process to change the desired fractions of fibers in the individual blowing devices in a way that diverges from the amounts actually needed for symmetry so that the subsequent migration processes of the fibers are taken into account.

The wound care article according to the invention can also have at least one flat layer containing cellulose fibers, foamed material, modified cellulose and/or alginates.

The term "foamed material" refers to an open-celled or close-celled foamed material, preferably made of polyurethane.

Modified celluloses are preferably derivatives of cellulose, preferably nanocelluloses, sulfonated and/or sulfoalkylated celluloses and their derivatives, preferably cellulose ethylsulfonates, carboxy-alkylated celluloses, preferably carboxymethyl cellulose, carboxyethyl cellulose and/or carboxypropyl cellulose, more complex cellulose derivatives such as sulpho-ethyl carboxymethyl cellulose, carboxymethyl hydroxyethyl cellulose, hydroxypropyl methyl cellulose, and amidated cellulose derivatives such as carboxymethyl cellulose amide or carboxypropyl cellulose amide. Carboxymethyl cellulose is present especially in the form of sodium carboxymethyl hydroxyethyl cellulose and is commercially available under the brand name "Hydrofiber". In hygiene and wound products, the fibers are incorporated into a flat matrix. Since they absorb fluid from the wound exudate, the fibers are gradually converted into a gel cushion that retains the fluid and does not release it again. In this context, the fibers are structured in such a way that the wound exudate is only absorbed in the vertical direction. This means that, as long as the capacity is sufficient, the exudate does not flow beyond the edge of the wound. In this manner, maceration of the wound edge can be effectively prevented. In this context, chitins, chitosans and their derivatives should also be understood as cellulose derivatives.

Alginates are obtained from the brown algae and woven to form a fibrous web. Chemically speaking, they are polysaccharides, specifically calcium and/or sodium salts of alginic acids. Alginates can absorb fluid up to 20 times their own weight, a process in which the wound exudate is stored in the cavities. The Ca2+ ions contained in the alginate mesh are exchanged for the Na+ ions from the exudate until the degree of saturation of Na ions in the alginate has been reached. In this process, the wound dressing swells up and the alginate fiber is converted into a gel body due to swelling of the fibers.

Moreover, it is preferably provided for the wound care article to have a sheath consisting at least partially of a fluid-permeable material. Such a sheath has a multifaceted function. Among other things, it can prevent the wound care article from adhering to the wound, it can prevent exudate from flowing back into the wound, it can have a hypoallergenic effect and can prevent maceration of the wound edge. The sheath is preferably at least partially closed off by a seam, for example, an adhesive seam or an ultrasonic seam, and it can comprise a foil or a film (for example, made of polyethylene) or else a nonwoven (for example, made of polypropylene) or fleece.

In particular, it can be provided for the sheath to have pores that, on average, are smaller than the superabsorbent particles. This can prevent particles from trickling out of the sheath. This can especially interfere with the sterilization process, namely, if particles get into the area of the sealing barrier where they might cause leaks.

The sheath can also be coated or mixed with a heavy metal in elementary or ion form, for example, silver, zinc or copper. The sheath can also be coated with a material that binds bacteria by means of hydrophobic interactions such as, for instance, dialkyl carbamoyl chloride (DACC).

The pore size, however, also influences the flow rate of the exudate that is to be absorbed. This applies especially to more or less hydrophobic polymer materials. A suitable avivage process can generally improve the wettability of the sheath, thereby ensuring the proper flow rate, even in case of small pores.

The pores or meshes of the sheath are preferably 0.05 mm to 1.0 mm n size, preferably 0.20 mm to 0.50 mm. Moreover, it can preferably be provided for the pores or mesh to be delimited by filament or fiber sections whose cross section through the sheath is approximately arch-shaped and whose arch apexes face outward.

Here, it is preferably provided that (i) in a top view, the flat layer has a surface area (F1) that, in the non-wetted state, is 3% to 75% smaller than the surface area (F2) of the interior provided by the sheath, and/or (ii) the sheath has material that is flexible, at least in certain sections.

In the first case, one speaks of a so-called expansion space that is formed by the sheath of the flat layer. Consequently, in both cases, it is ensured that the sheath does not offer any resistance to the volume increase of the flat layer that is caused by the absorption of fluid, so that the layer can develop its full absorption capacity. The flexible material can contain, for instance, Lycra, Elasthane, polypropylene, rubber, latex, nylon or the like.

Moreover, it is preferably provided for the sheath to consist at least partially of a three-dimensional wound spacer mesh or to be lined or underlined with it. Said wound spacer mesh is preferably made of a polyethylene film by means of a blow-molding process as is described, for instance, in European patent application EP 2004116 A1. By the same token, for example, it can be a silicone mesh.

Such a mesh also has a wide array of functions. Depending on the configuration of the pores, it can perform a valve function, thereby preventing exudate from flowing back (especially if the pores are configured so as to be funnel-shaped or collar-shaped). It can prevent the wound care article from adhering to the wound (preferably by using a silicone material). In case of an appropriate arrangement, such a mesh can have abrasive properties and thus transfer the biofilms to the wound or prevent their formation (especially if the pores are configured so as to be funnel-shaped or collar-shaped). It can also have anti-hemorrhagic properties and, in certain cases, it can be capable of immobilizing or binding bacteria by means of static interactions (especially with the use of a polyethylene material or of a material with a positive net charge). Furthermore, the surface can be functionalized, for example, with a silver or silicone coating.

Moreover, it is provided for the sheath to consist at least partially of an impregnated or water-impermeable material or to be lined or underlined with it. This can be a colored or conspicuously designed wash protection (backsheet).

Moreover, it is also provided for the wound care article to contain a fraction of at least one heavy metal in elementary or ion form. In the most finely dispersed form, heavy metals have a bactericidal effect, which, due to the large reactive surface area, can be ascribed to the sufficient formation of soluble heavy metal ions.

Doping with at least one heavy metal in elementary or ion form can give the primary bandage an antibacterial effect, which can reduce complications in the case of infection-prone wounds (decubitus, Ulcus cruris, burn wounds, etc.) and can, at the same time, increase the time during which the wound dressing can remain in place.

It is preferably provided for the at least one heavy metal in elementary or ion form to be selected from the group containing copper, zinc and/or silver. The above-mentioned bactericidal properties hold true especially for these three metals.

Moreover, it is preferably provided for the flat layer or the sheath to be lined or replaced by a cover film on at least one side. Preferably, said cover film has at least one of the following properties:
adhesive coating
fluid-tightness
water-vapor-permeability and/or
flexibility.

In this context, it is preferably provided for the cover film to extend beyond the periphery of the wound care article and for it to be applied to the skin surrounding the wound. This yields a so-called border or island dressing.

As an alternative, it is provided for the sheath itself to have an adhesive coating on at least one side. In the above-mentioned cases, the adhesive coating is preferably an acrylate adhesive, a silicone adhesive, a starch adhesive, a hydrocolloid adhesive and/or any other suitable physiologically safe adhesive.

The wound care article can also have at least one component selected from the group containing:
hyaluronic acid (preferably as a sheathing for superabsorbent polymers)
octenidine
dimethicone
activated charcoal.

Furthermore, according to the invention, the following is provided:
a) the use of a wound care article according to one of the preceding claims in a negative-pressure wound care system, and
b) the use of a wound care article according to one of the preceding claims for the treatment of acute and post-intervention wounds, chronic wounds, diabetic wounds or pressure ulcers, tumor wounds, burns, slightly to highly exuding wounds, as well as deep wounds that need defect filling.

The use in the sacral region is particularly preferred.

The nonwoven according to the invention can be produced as follows:

1. Dry Spinning

Superabsorbent fibers with a thickness of 10 dtex and made of a copolymer having the above-mentioned composition are produced by dry spinning from an aqueous solution and by cutting (staple length of 6 mm), after which they are cross-linked at 200° C. until ester bridges are formed between the carboxylic acid groups and the hydroxyl groups. The superabsorbent fibers displayed an absorption capacity of 50 g/g (measured by the Free Swell Absorbency Test) and a retention under load of 35 g/g.

2. Wet-Laid Process

A Pulp Evaluation Apparatus made by the Mavis Manufacturing Company, London, England was used to make wet-laid nonwovens. All of the nonwovens were produced as sheets with a dry weight of 1.2 grams. The requisite amount of dry cellulose (Rayon XF grade) was dispersed at 5000 rpm in 2 liters of water using a high-shear mixer. The cellulose fiber exhibited an absorption capacity of less than 10 g/g retention, measured by centrifugation of a 0.9%-by-weight saline solution. The superabsorbent fiber was dispersed in 100 ml of water for a few seconds until it had swelled, and then it was added to the dispersed cellulose fiber. The mixture was stirred with a spatula. The mixture was then added to a column for paper production and the nonwoven was shaped on a 25-mesh screen. The fibers were compressed and dried at room temperature. This yielded sheets having the following properties.

|  | % superabsorbent fibers | % by weight cellulose (g) | % by weight superabsorbent fibers | absorption of 0.9%-saline solution (g/g) (Free Swell Absorbency Test) | Retention under load (g/g) |
| --- | --- | --- | --- | --- | --- |
| Control | 0 | 1.20 | 0 | 9.79 | 8.14 |
| Example 1 | 5 | 1.14 | 0.06 | 10.59 | 9.48 |
| Example 2 | 10 | 1.08 | 0.12 | 11.04 | 10.04 |
| Example 3 | 20 | 0.96 | 0.24 | 12.88 | 10.56 |

FIG. 1 shows a nonwoven according to the invention in a scanning electron microscope image. Here, A designates the superabsorbent fibers, B designates the superabsorbent particles, and C designates a cushioning layer of cellulose fibers with air in-between ("Fluff Pulp") (D).

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A wound care article comprising at least one flat layer in a form of a woven fabric or nonwoven fabric, wherein said woven fabric or nonwoven fabric comprises
   (i) a thermobonded matrix of fibers including superabsorbent fibers, and bi-component fibers, and
   (ii) superabsorbent particles embedded in said matrix of fibers,
   wherein the superabsorbent fibers consist of a superabsorbent cross-linked polymer,
   wherein said bi-component fibers comprise a first polymer and a second polymer having different physical-chemical properties that have been co-extruded in a sheath/core configuration or a side-by-side configuration, neither of said first polymer and said second polymer being a superabsorbent polymer,
   wherein said first polymer is a thermoplastic polymer having a melting point that is lower than a melting point of said second polymer, and
   wherein said first polymer functions as a hot-melt adhesive that facilitates thermobonding of the matrix of fibers.

2. The wound care article according to claim 1, wherein the superabsorbent cross-linked polymer is made up at least of monomer constituents
   acrylic acid or acrylate ("AA"),
   methylacrylate or methylacrylic acid ("MA"), and
   acrylic acid or methylacrylic acid that is partially neutralized to form a partial sodium salt ("AA-Na"), and
   wherein ester bonds cross-link individual polymer chains of the cross-linked polymer, and
   wherein the ester bonds are between acid groups of the "AA", the "MA", and the "AA-Na".

3. The wound care article according to claim 2, wherein the at least one flat layer further comprises cellulose fibers.

4. The wound care article according to claim 3, wherein the at least one flat layer is lined or underlined with a thin nonwoven fabric on at least one side.

5. The wound care article according to claim 1, wherein the wound care article has a symmetrical layer structure.

6. The wound care article according to claim 5, further comprising at least one other flat layer containing one or more of cellulose fibers, foamed material, modified cellulose and alginates.

7. The wound care article according to claim 6, further comprising a sheath that at least partially comprises a fluid-permeable material.

8. The wound care article according to claim 7, wherein
(i) in a top view, the at least one flat layer has a surface area (F1) that, in a non-wetted state, is 3% to 75% smaller than a surface area (F2) of an interior provided by the sheath, and
(ii) the sheath has material that is flexible at least in certain sections.

9. The wound care article according to claim 7, wherein the sheath at least partially comprises a three-dimensional wound spacer mesh or is lined or underlined with the three-dimensional wound spacer mesh.

10. The wound care article according to claim 7, the sheath at least partially comprises an impregnated or water-impermeable material or is lined or underlined with the impregnated or water-impermeable material.

11. The wound care article according to claim 10, further comprising a fraction comprising at least one heavy metal in elementary or ion form.

12. The wound care article according to claim 10, the at least one heavy metal in elementary or ion form is selected from the group containing copper, zinc and silver.

13. The wound care article according to claim 10, wherein the at least one flat layer or the sheath is lined with a cover film on at least one side.

14. The wound care article according to claim 13, wherein the cover film extends beyond a periphery of the wound care article such that it is applicable to skin surrounding a wound.

15. The wound care article according to claim 10, wherein the at least one flat layer or the sheath has an adhesive coating on at least one side.

16. A method of using a wound care article according to claim 1, the method comprising: coupling the wound care article of claim 1 in a negative-pressure wound care system.

17. A method of using a wound care article according to claim 1, the method comprising: treating a patient with the wound care article of claim 1 for acute and post-intervention wounds, chronic wounds, diabetic wounds or pressure ulcers, tumor wounds, burns, slightly to highly exuding wounds, and deep wounds that need defect filling.

* * * * *